(12) United States Patent
Goldor et al.

(10) Patent No.: US 9,404,490 B2
(45) Date of Patent: *Aug. 2, 2016

(54) FINGER-TYPE PERISTALTIC PUMP (71) Applicant: Q-CORE MEDICAL LTD., Netanya (IL)

(72) Inventors: Ori Goldor, Givat Ada (IL); Shachar Rotem, M.P. Hefer (IL)

(73) Assignee: Q-CORE MEDICAL LTD., Netanya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/181,673

(22) Filed: Feb. 16, 2014

(65) Prior Publication Data

US 2014/0369872 A1 Dec. 18, 2014

Related U.S. Application Data

(63) Continuation of application No. 13/229,798, filed on Sep. 12, 2011, now Pat. No. 8,678,793, which is a continuation of application No. 11/791,599, filed as application No. PCT/IL2005/001249 on Nov. 24, 2005, now Pat. No. 8,029,253.

(30) Foreign Application Priority Data

Nov. 24, 2004 (IL) .......................................... 165365

(51) Int. Cl.
*F04B 43/02* (2006.01)
*F04B 43/12* (2006.01)
(Continued)

(52) U.S. Cl.
CPC ............ *F04B 43/12* (2013.01); *A61M 5/14228* (2013.01); *F04B 43/082* (2013.01); *A61M 39/281* (2013.01)

(58) Field of Classification Search
CPC .............. A61M 39/28; A61M 39/281; A61M 2205/14; F04B 43/08; F04B 43/082
See application file for complete search history.

(56) References Cited

U.S. PATENT DOCUMENTS 2,056,322 A 10/1936 Hoppe
2,393,838 A 1/1946 Tarbox
(Continued)

FOREIGN PATENT DOCUMENTS

DE 10118086 A1 7/2002
EP 0215249 A1 3/1987
(Continued)

OTHER PUBLICATIONS

Honeywell Sensing and Control, "FSSI500NSB force sensor", Golden Valley, Minnesota, USA, 1998-2004 http://sccatalog.honeywell.com/imc/printfriendly.asp?FAM~force&PN~FSSI500NSB (5 pages).
(Continued)

*Primary Examiner* — Patrick Hamo
(74) *Attorney, Agent, or Firm* — Professional Patent Solutions; Vladimir Sherman (57) ABSTRACT

The invention provides a finger-type peristaltic pump (2) having a body (4) and a housing (6). The body contains two or more finger-type valves (16) and a processor (22) configured to operate the valves according to a predetermined temporospatial pattern. The housing has a passageway (18) configured to receive a conduit. The housing has a first position in which a conduit in the passageway is positioned adjacent to the valve fingers, and a second position in which a conduit in the passageway is not adjacent to the valve fingers. The invention also provides a housing for use in the pump of the invention.

17 Claims, 5 Drawing Sheets

(51) Int. Cl.
 *A61M 5/142* (2006.01)
 *F04B 43/08* (2006.01)
 *A61M 39/28* (2006.01)

(56) References Cited

U.S. PATENT DOCUMENTS

| | | | |
|---|---|---|---|
| 2,743,898 A | 5/1956 | King |
| 2,981,115 A | 4/1961 | Beguin |
| 3,443,585 A | 5/1969 | Reinicke |
| 3,511,583 A | 5/1970 | Brown |
| 3,677,667 A | 7/1972 | Morrison |
| 3,778,195 A | 12/1973 | Bamberg |
| 3,843,796 A | 10/1974 | Miller |
| 3,846,553 A | 11/1974 | Shen et al. |
| 3,856,956 A | 12/1974 | Oxley et al. |
| 3,876,786 A | 4/1975 | McEvoy et al. |
| 3,876,787 A | 4/1975 | McEvoy et al. |
| 3,891,699 A | 6/1975 | Witzel et al. |
| 3,928,135 A | 12/1975 | Milner |
| 3,982,722 A | 9/1976 | Bernard |
| 3,982,725 A | 9/1976 | Clark |
| 4,001,280 A | 1/1977 | Umio et al. |
| 4,014,318 A | 3/1977 | Dockum et al. |
| 4,029,770 A | 6/1977 | Willard, Sr. |
| 4,029,788 A | 6/1977 | Fabio et al. |
| 4,039,269 A | 8/1977 | Pickering |
| 4,048,314 A | 9/1977 | Kubela et al. |
| 4,048,332 A | 9/1977 | Adams et al. |
| 4,112,095 A | 9/1978 | Allen, Jr. et al. |
| 4,115,572 A | 9/1978 | Paul et al. |
| 4,117,130 A | 9/1978 | Allen, Jr. et al. |
| 4,155,362 A | 5/1979 | Jess |
| 4,159,375 A | 6/1979 | Trust et al. |
| 4,236,880 A | 12/1980 | Archibald |
| 4,243,609 A | 1/1981 | Shepherd |
| 4,243,658 A | 1/1981 | Chang |
| 4,243,681 A | 1/1981 | Morrow et al. |
| 4,244,142 A | 1/1981 | Crawford |
| 4,244,944 A | 1/1981 | Wilkinson |
| 4,244,945 A | 1/1981 | Wilkinson |
| 4,244,953 A | 1/1981 | Trust et al. |
| 4,244,968 A | 1/1981 | Friedmann |
| 4,244,969 A | 1/1981 | Carlsson et al. |
| 4,245,097 A | 1/1981 | Shepherd |
| 4,245,119 A | 1/1981 | Shepherd |
| 4,245,120 A | 1/1981 | Shepherd |
| 4,246,272 A | 1/1981 | Noel |
| 4,270,532 A | 6/1981 | Franetzki et al. |
| 4,320,781 A | 3/1982 | Bouvet et al. |
| 4,373,525 A | 2/1983 | Kobayashi |
| 4,450,375 A | 5/1984 | Siegal |
| 4,489,863 A | 12/1984 | Horchos et al. |
| 4,493,706 A | 1/1985 | Borsanyi et al. |
| 4,650,469 A | 3/1987 | Berg et al. |
| 4,671,792 A | 6/1987 | Borsanyi |
| 4,682,135 A | 7/1987 | Yamakawa |
| 4,690,673 A | 9/1987 | Bloomquist |
| 4,725,205 A | 2/1988 | Cannon et al. |
| 4,728,265 A | 3/1988 | Cannon |
| 4,741,736 A | 5/1988 | Brown |
| 4,748,003 A | 5/1988 | Riley |
| 4,755,168 A | 7/1988 | Romanelli et al. |
| 4,770,410 A | 9/1988 | Brown |
| 4,836,752 A | 6/1989 | Burkett |
| 4,852,585 A | 8/1989 | Heath |
| 4,867,744 A | 9/1989 | Borsanyi |
| 4,867,973 A | 9/1989 | Goers et al. |
| 4,893,991 A | 1/1990 | Heminway et al. |
| 4,927,411 A | 5/1990 | Pastrone et al. |
| 4,954,046 A | 9/1990 | Irvin et al. |
| 4,954,256 A | 9/1990 | Degen et al. |
| 4,972,535 A | 11/1990 | Goldman |
| 4,978,335 A | 12/1990 | Arthur, III |
| 5,074,756 A | 12/1991 | Davis |
| 5,078,683 A | 1/1992 | Sancoff et al. |
| 5,088,904 A | 2/1992 | Okada |
| 5,096,385 A | 3/1992 | Georgi et al. |
| 5,103,211 A | 4/1992 | Daoud et al. |
| 5,151,019 A | 9/1992 | Danby et al. |
| 5,152,680 A | 10/1992 | Okada |
| 5,165,874 A * | 11/1992 | Sancoff et al. ............... 417/474 |
| 5,213,483 A | 5/1993 | Flaherty et al. |
| 5,219,327 A | 6/1993 | Okada |
| 5,222,946 A | 6/1993 | Kamen |
| 5,246,347 A | 9/1993 | Davis |
| 5,257,978 A | 11/1993 | Haber et al. |
| 5,269,304 A | 12/1993 | Matthews |
| 5,271,735 A | 12/1993 | Greenfeld et al. |
| 5,286,176 A | 2/1994 | Bonin |
| 5,290,158 A | 3/1994 | Okada |
| 5,308,333 A | 5/1994 | Skakoon |
| 5,334,315 A | 8/1994 | Matkovich et al. |
| 5,338,157 A | 8/1994 | Blomquist |
| 5,395,320 A | 3/1995 | Padda et al. |
| 5,429,485 A | 7/1995 | Dodge |
| 5,443,442 A | 8/1995 | Phipps et al. |
| 5,485,408 A | 1/1996 | Blomquist |
| 5,499,969 A | 3/1996 | Beuchat et al. |
| 5,509,439 A | 4/1996 | Tantardini |
| 5,527,295 A | 6/1996 | Wing |
| 5,542,826 A | 8/1996 | Warner |
| 5,556,746 A | 9/1996 | Herrmann et al. |
| 5,569,188 A | 10/1996 | Mackool |
| 5,575,309 A | 11/1996 | Connell |
| 5,575,631 A | 11/1996 | Jester |
| 5,577,891 A | 11/1996 | Loughnane et al. |
| 5,584,667 A | 12/1996 | Davis |
| 5,591,124 A | 1/1997 | Phipps |
| 5,593,134 A | 1/1997 | Steber et al. |
| 5,601,420 A | 2/1997 | Warner et al. |
| 5,609,770 A | 3/1997 | Zimmerman et al. |
| 5,622,530 A | 4/1997 | Phipps |
| 5,628,619 A | 5/1997 | Wilson |
| 5,652,274 A | 7/1997 | Martin |
| 5,658,250 A | 8/1997 | Blomquist et al. |
| 5,658,252 A | 8/1997 | Johnson |
| 5,660,529 A | 8/1997 | Hill |
| 5,669,877 A | 9/1997 | Blomquist |
| 5,677,181 A | 10/1997 | Parish |
| 5,683,233 A | 11/1997 | Moubayed et al. |
| 5,695,473 A | 12/1997 | Olsen |
| 5,704,584 A | 1/1998 | Winterer et al. |
| 5,728,393 A | 3/1998 | Soudant et al. |
| 5,742,519 A | 4/1998 | McClendon et al. |
| 5,782,805 A | 7/1998 | Meinzer et al. |
| 5,788,669 A | 8/1998 | Peterson |
| 5,791,880 A | 8/1998 | Wilson |
| 5,791,881 A | 8/1998 | Moubayed et al. |
| 5,803,712 A | 9/1998 | Davis et al. |
| 5,807,322 A | 9/1998 | Lindsey et al. |
| 5,810,323 A | 9/1998 | Winterer et al. |
| 5,853,386 A | 12/1998 | Davis et al. |
| 5,874,081 A | 2/1999 | Parish |
| 5,876,370 A | 3/1999 | Blomquist |
| 5,888,052 A | 3/1999 | Hill |
| 5,896,076 A | 4/1999 | Van Namen |
| 5,909,724 A | 6/1999 | Nishimura et al. |
| 5,924,852 A | 7/1999 | Moubayed et al. |
| 5,935,099 A | 8/1999 | Peterson et al. |
| 5,935,106 A | 8/1999 | Olsen |
| 5,943,633 A | 8/1999 | Wilson et al. |
| 5,954,485 A | 9/1999 | Johnson et al. |
| 5,980,490 A | 11/1999 | Tsoukalis |
| 5,996,964 A | 12/1999 | Ben-Shalom |
| 6,004,309 A | 12/1999 | Phipps |
| 6,004,583 A | 12/1999 | Platé et al. |
| 6,024,539 A | 2/2000 | Blomquist |
| 6,095,189 A | 8/2000 | Ben-Shalom |
| 6,110,153 A | 8/2000 | Davis et al. |
| 6,143,530 A | 11/2000 | Crouzet et al. |
| 6,146,109 A | 11/2000 | Davis et al. |
| 6,164,921 A | 12/2000 | Moubayed et al. |
| 6,165,874 A | 12/2000 | Powell et al. |
| RE37,074 E | 2/2001 | Danby et al. |

(56) References Cited

U.S. PATENT DOCUMENTS

| | | | |
|---|---|---|---|
| 6,203,296 B1 | 3/2001 | Ray et al. |
| 6,213,723 B1 | 4/2001 | Danby et al. |
| 6,213,739 B1 | 4/2001 | Phallen et al. |
| 6,234,773 B1 | 5/2001 | Hill et al. |
| 6,238,320 B1 | 5/2001 | Flanagan |
| 6,241,704 B1 | 6/2001 | Peterson et al. |
| 6,261,262 B1 | 7/2001 | Briggs et al. |
| 6,280,408 B1 | 8/2001 | Sipin |
| 6,312,227 B1 | 11/2001 | Davis |
| 6,339,410 B1 | 1/2002 | Milner et al. |
| 6,347,553 B1 | 2/2002 | Morris et al. |
| 6,371,732 B1 | 4/2002 | Moubayed et al. |
| 6,422,057 B1 | 7/2002 | Anderson |
| 6,450,773 B1 | 9/2002 | Upton |
| 6,475,180 B2 | 11/2002 | Peterson et al. |
| 6,519,569 B1 | 2/2003 | White et al. |
| 6,537,244 B2 | 3/2003 | Paukovits et al. |
| 6,544,171 B2 | 4/2003 | Beetz et al. |
| 6,558,347 B1 | 5/2003 | Jhuboo et al. |
| 6,572,604 B1 | 6/2003 | Platt et al. |
| 6,622,542 B2 | 9/2003 | Derek et al. |
| 6,648,861 B2 | 11/2003 | Platt et al. |
| 6,692,241 B2 | 2/2004 | Watanabe et al. |
| 6,733,476 B2 | 5/2004 | Christenson et al. |
| 6,742,992 B2 | 6/2004 | Davis |
| 6,749,587 B2 | 6/2004 | Flaherty |
| 6,768,425 B2 | 7/2004 | Flaherty et al. |
| 6,788,199 B2 | 9/2004 | Crabtree et al. |
| 6,790,198 B1 | 9/2004 | White et al. |
| 6,902,549 B2 | 6/2005 | Marmaropoulos et al. |
| 6,942,473 B2 | 9/2005 | Abrahamson et al. |
| 7,018,361 B2 | 3/2006 | Gillespie, Jr. et al. |
| 7,022,075 B2 | 4/2006 | Grunwald et al. |
| 7,048,720 B1 | 5/2006 | Thorne, Jr. et al. |
| 7,059,840 B2 | 6/2006 | Corwin et al. |
| 7,122,026 B2 | 10/2006 | Rogers et al. |
| 7,131,966 B1 | 11/2006 | Tamari |
| 7,163,385 B2 | 1/2007 | Gharib et al. |
| 7,347,836 B2 | 3/2008 | Peterson et al. |
| 7,525,432 B2 | 4/2009 | Jackson |
| 7,556,481 B2 | 7/2009 | Moubayed |
| 7,645,258 B2 | 1/2010 | White et al. |
| 7,654,976 B2 | 2/2010 | Peterson et al. |
| 7,695,255 B2 * | 4/2010 | Ben-Shalom et al. ........ 417/412 |
| 7,698,156 B2 | 4/2010 | Martucci et al. |
| 7,704,227 B2 | 4/2010 | Moberg et al. |
| 7,762,795 B2 | 7/2010 | Moubayed |
| 7,840,260 B2 | 11/2010 | Epley |
| 7,892,332 B2 | 2/2011 | Prisco et al. |
| 7,896,834 B2 | 3/2011 | Smisson, III et al. |
| 7,935,102 B2 | 5/2011 | Breznock et al. |
| 7,938,796 B2 | 5/2011 | Moubayed et al. |
| 7,963,946 B2 | 6/2011 | Moubayed et al. |
| 7,998,121 B2 | 8/2011 | Stringham |
| 8,025,634 B1 | 9/2011 | Moubayed et al. |
| 8,029,253 B2 | 10/2011 | Rotem et al. |
| 8,142,400 B2 | 3/2012 | Rotem et al. |
| 8,182,445 B2 | 5/2012 | Moubayed et al. |
| 8,197,235 B2 | 6/2012 | Davis |
| 8,214,231 B2 | 7/2012 | Martucci et al. |
| 8,234,128 B2 | 7/2012 | Martucci et al. |
| 8,241,018 B2 | 8/2012 | Harr |
| 8,257,654 B2 | 9/2012 | Maus et al. |
| 8,308,457 B2 | 11/2012 | Rotem et al. |
| 8,334,768 B2 | 12/2012 | Eaton et al. |
| 8,337,168 B2 | 12/2012 | Rotem et al. |
| 8,343,111 B2 | 1/2013 | Beck et al. |
| 8,352,290 B2 | 1/2013 | Bartz et al. |
| 8,363,583 B2 | 1/2013 | Jia et al. |
| 8,371,832 B2 | 2/2013 | Rotem et al. |
| 8,444,587 B2 | 5/2013 | Kelly et al. |
| 8,489,427 B2 | 7/2013 | Simpson et al. |
| 8,535,025 B2 | 9/2013 | Rotem et al. |
| 8,579,816 B2 | 11/2013 | Kamath et al. |
| 8,666,367 B2 | 3/2014 | Sharp et al. |
| 8,672,875 B2 | 3/2014 | Vanderveen et al. |
| 8,678,793 B2 | 3/2014 | Goldor et al. |
| 8,920,144 B2 | 12/2014 | Rotem et al. |
| 9,056,160 B2 | 6/2015 | Rotem et al. |
| 2001/0029321 A1 | 10/2001 | Beetz et al. |
| 2002/0056675 A1 | 5/2002 | Hegde |
| 2002/0094287 A1 | 7/2002 | Davis |
| 2002/0156402 A1 | 10/2002 | Woog et al. |
| 2002/0165503 A1 | 11/2002 | Morris et al. |
| 2003/0034887 A1 | 2/2003 | Crabtree et al. |
| 2003/0040700 A1 | 2/2003 | Hickle et al. |
| 2003/0065536 A1 | 4/2003 | Hansen et al. |
| 2003/0109988 A1 | 6/2003 | Geissler et al. |
| 2003/0140928 A1 | 7/2003 | Bui et al. |
| 2003/0141981 A1 | 7/2003 | Bui et al. |
| 2003/0182586 A1 | 9/2003 | Numano |
| 2004/0167804 A1 | 8/2004 | Simpson et al. |
| 2004/0172222 A1 | 9/2004 | Simpson et al. |
| 2004/0181314 A1 | 9/2004 | Zaleski |
| 2004/0191112 A1 | 9/2004 | Hill et al. |
| 2004/0204673 A1 | 10/2004 | Flaherty |
| 2004/0204685 A1 | 10/2004 | Wright et al. |
| 2004/0235446 A1 | 11/2004 | Flaherty et al. |
| 2005/0001369 A1 | 1/2005 | Cross |
| 2005/0022274 A1 | 1/2005 | Campbell et al. |
| 2005/0055242 A1 | 3/2005 | Bello et al. |
| 2005/0088409 A1 | 4/2005 | Van Berkel |
| 2005/0112001 A1 | 5/2005 | Bahnen et al. |
| 2005/0171501 A1 | 8/2005 | Kelly |
| 2005/0191196 A1 | 9/2005 | Tanner et al. |
| 2005/0214146 A1 | 9/2005 | Corwin et al. |
| 2006/0051218 A1 | 3/2006 | Harttig |
| 2006/0083644 A1 | 4/2006 | Zumbrum et al. |
| 2006/0173419 A1 | 8/2006 | Malcolm |
| 2006/0213249 A1 | 9/2006 | Uram et al. |
| 2007/0032098 A1 | 2/2007 | Bowles et al. |
| 2007/0048161 A1 | 3/2007 | Moubayed |
| 2007/0060872 A1 | 3/2007 | Hall et al. |
| 2007/0118405 A1 | 5/2007 | Campbell et al. |
| 2007/0135866 A1 | 6/2007 | Baker et al. |
| 2007/0154336 A1 | 7/2007 | Miyazaki et al. |
| 2007/0217931 A1 | 9/2007 | Estes et al. |
| 2007/0269324 A1 | 11/2007 | Goldor et al. |
| 2008/0015506 A1 | 1/2008 | Davis |
| 2008/0065007 A1 | 3/2008 | Peterson et al. |
| 2008/0065016 A1 | 3/2008 | Peterson et al. |
| 2008/0067462 A1 | 3/2008 | Miller et al. |
| 2008/0071251 A1 | 3/2008 | Moubayed et al. |
| 2008/0095649 A1 | 4/2008 | Ben-Shalom et al. |
| 2008/0144560 A1 | 6/2008 | Jia et al. |
| 2008/0145249 A1 | 6/2008 | Smisson et al. |
| 2008/0146995 A1 | 6/2008 | Smisson et al. |
| 2008/0275307 A1 | 11/2008 | Poschmann |
| 2009/0088675 A1 | 4/2009 | Kelly et al. |
| 2009/0163864 A1 | 6/2009 | Breznock et al. |
| 2009/0203329 A1 | 8/2009 | White et al. |
| 2009/0221964 A1 | 9/2009 | Rotem et al. |
| 2009/0240201 A1 | 9/2009 | Rotem et al. |
| 2009/0270810 A1 | 10/2009 | DeBelser et al. |
| 2009/0300507 A1 | 12/2009 | Raghavan et al. |
| 2009/0317268 A1 | 12/2009 | Rotem et al. |
| 2010/0016781 A1 | 1/2010 | Nakayama et al. |
| 2010/0036322 A1 | 2/2010 | Rotem |
| 2010/0082001 A1 | 4/2010 | Beck et al. |
| 2010/0168545 A1 | 7/2010 | Kamath et al. |
| 2010/0211002 A1 | 8/2010 | Davis |
| 2010/0228223 A1 | 9/2010 | Williams et al. |
| 2010/0234708 A1 | 9/2010 | Buck et al. |
| 2010/0279652 A1 | 11/2010 | Sharp et al. |
| 2011/0148624 A1 | 6/2011 | Eaton et al. |
| 2011/0152772 A1 | 6/2011 | Rotem et al. |
| 2011/0152831 A1 | 6/2011 | Rotem et al. |
| 2011/0167133 A1 | 7/2011 | Jain |
| 2011/0251856 A1 | 10/2011 | Maus et al. |
| 2011/0264043 A1 | 10/2011 | Kotnik et al. |
| 2011/0276000 A1 | 11/2011 | Stringham |
| 2011/0282291 A1 | 11/2011 | Ciccone |
| 2011/0318208 A1 | 12/2011 | Goldor et al. |
| 2012/0059389 A1 | 3/2012 | Larson et al. |

(56) References Cited

U.S. PATENT DOCUMENTS

| | | |
|---|---|---|
| 2012/0062387 A1 | 3/2012 | Vik et al. |
| 2012/0136305 A1 | 5/2012 | Gagliardoni et al. |
| 2012/0241525 A1 | 9/2012 | Borges et al. |
| 2013/0006666 A1 | 1/2013 | Schneider et al. |
| 2013/0046508 A1 | 2/2013 | Sur et al. |
| 2013/0116620 A1 | 5/2013 | Rotem et al. |
| 2013/0116623 A1 | 5/2013 | Rotem et al. |
| 2013/0142670 A1 | 6/2013 | Rotem et al. |
| 2013/0209275 A1 | 8/2013 | Rotem et al. |
| 2013/0345623 A1 | 12/2013 | Kopperschmidt et al. |
| 2014/0005631 A1 | 1/2014 | Rotem et al. |
| 2014/0119954 A1 | 5/2014 | Schweitzer et al. |
| 2014/0197824 A1 | 7/2014 | Gillespie et al. |
| 2014/0222377 A1 | 8/2014 | Bitan et al. |
| 2014/0276564 A1 | 9/2014 | Schneider |
| 2014/0369872 A1 | 12/2014 | Goldor et al. |
| 2014/0378901 A1 | 12/2014 | Rotem et al. |
| 2015/0038187 A1 | 2/2015 | Ho et al. |
| 2015/0073338 A1 | 3/2015 | Waldhoff et al. |
| 2015/0105726 A1 | 4/2015 | Qi et al. |
| 2015/0137988 A1 | 5/2015 | Gravenstein et al. |
| 2015/0141955 A1 | 5/2015 | Ruchti et al. |
| 2015/0172921 A1 | 6/2015 | Wang et al. |
| 2015/0182694 A1 | 7/2015 | Rosinko |
| 2015/0192120 A1 | 7/2015 | Rotem et al. |

FOREIGN PATENT DOCUMENTS

| | | |
|---|---|---|
| EP | 0225158 A2 | 6/1987 |
| EP | 0315312 A1 | 5/1989 |
| EP | 0429866 A1 | 6/1991 |
| EP | 0483794 A1 | 5/1992 |
| EP | 0858812 A2 | 8/1998 |
| EP | 1031358 A1 | 8/2000 |
| EP | 1350955 A2 | 10/2003 |
| EP | 1557186 | 7/2005 |
| EP | 1611834 A2 | 1/2006 |
| EP | 1485149 B1 | 7/2008 |
| FR | 2632529 A1 | 12/1989 |
| FR | 2753236 A1 | 3/1998 |
| JP | 60043188 A | 3/1985 |
| JP | 6-169992 A | 6/1994 |
| JP | 2002-57738 A | 2/2002 |
| JP | 2004141418 A | 5/2004 |
| WO | 8400691 A1 | 3/1984 |
| WO | 9116933 A1 | 11/1991 |
| WO | 9325816 A1 | 12/1993 |
| WO | 9408647 A1 | 4/1994 |
| WO | 9603168 A1 | 2/1996 |
| WO | 9630679 A1 | 10/1996 |
| WO | 9734084 A1 | 9/1997 |
| WO | 9804301 A1 | 2/1998 |
| WO | 9813080 A2 | 4/1998 |
| WO | 9847551 A1 | 10/1998 |
| WO | 99/58178 A1 | 11/1999 |
| WO | 9958178 A1 | 11/1999 |
| WO | 0139816 A2 | 6/2001 |
| WO | 0165232 A1 | 9/2001 |
| WO | 0236044 A2 | 5/2002 |
| WO | 0238204 A2 | 5/2002 |
| WO | 0249509 A2 | 6/2002 |
| WO | 0268015 A2 | 9/2002 |
| WO | 03027503 A1 | 4/2003 |
| WO | 03080158 A1 | 10/2003 |
| WO | 2004070548 A2 | 8/2004 |
| WO | 2004093648 A2 | 11/2004 |
| WO | 2005089263 A2 | 9/2005 |
| WO | 2006/056986 A1 | 6/2006 |
| WO | 2006056986 A1 | 6/2006 |
| WO | 2007133259 A1 | 11/2007 |
| WO | 2008036658 A2 | 3/2008 |
| WO | 2008059492 A2 | 5/2008 |
| WO | 2008059493 A2 | 5/2008 |
| WO | 2008059494 A2 | 5/2008 |
| WO | 2008059495 A2 | 5/2008 |
| WO | 2008059496 A2 | 5/2008 |
| WO | 2008059498 A2 | 5/2008 |
| WO | 2008059499 A2 | 5/2008 |
| WO | 2008130644 A1 | 10/2008 |
| WO | 2010053702 A1 | 5/2010 |
| WO | 2010053703 A1 | 5/2010 |
| WO | 2010091313 A2 | 8/2010 |
| WO | 2011128850 A2 | 10/2011 |
| WO | 2012095827 A1 | 7/2012 |
| WO | 2012095829 A2 | 7/2012 |
| WO | 2013001425 A2 | 1/2013 |
| WO | 2013/028704 A1 | 2/2013 |
| WO | 2013028704 A1 | 2/2013 |
| WO | 2013/090748 A1 | 6/2013 |
| WO | 2013090748 A1 | 6/2013 |

OTHER PUBLICATIONS

International Application PCT/IL2007/001398 Search Report dated Jun. 11, 2008 (2 pages).

International Application PCT/IL2007/001398 Patentability Report dated May 19, 2009 (6 pages).

International Application PCT/IL2007/001399 Search Report dated Jun. 4, 2008 (3 pages).

International Application PCT/IL2007/001399 Patentability Report dated May 19, 2009 (9 pages).

International Application PCT/IL2007/001400 Search Report dated Jul. 15, 2008 (3 pages).

International Application PCT/IL2007/001400 Patentability Report dated May 19, 2009 (10 pages).

International Application PCT/IL2007/001401 Search Report dated Sep. 24, 2008 (2 pages).

International Application PCT/IL2007/001401 Patentability Report dated May 19, 2009 (11 pages).

International Application PCT/IL2007/001402 Search Report dated Jun. 20, 2008 (3 pages).

International Application PCT/IL2007/001402 Patentability Report dated May 19, 2009 (4 pages).

International Application PCT/IL2007/001404 Search Report dated Jul. 14, 2008 (2 pages).

International Application PCT/IL2007/001404 Patentability Report dated May 19, 2009 (7 pages).

International Application PCT/IL2007/001405 Search Report dated Jul. 21, 2008 (4 pages).

International Application PCT/IL2007/001405 Patentability Report dated May 19, 2009 (7 pages).

International Application PCT/IL2005/001249 Search Report dated Apr. 5, 2006 (18 pages).

International Application PCT/IL1997/000289 Search report dated Jan. 27, 1998 (18 pages).

International Application PCT/IL1997/000290 Search Report dated Jan. 27, 1998 (18 pages).

International Application PCT/IL2003/000947 Search Report dated Mar. 3, 2004 (43 pages).

International Application PCT/IB2011/051586 Search Report dated Oct. 27, 2011 (3 pages).

International Application PCT/IB2011/051586 Patentability Report dated Oct. 16, 2012 (9 pages).

International Application PCT/IB2012/050192 Search Report dated Aug. 17, 2012 (2 pages).

International Application PCT/IB2012/050192 Patentability Report dated Jul. 16, 2013 (6 pages).

International Application PCT/IB2012/050189 Search Report dated May 30, 2012 (2 pages).

International Application PCT/IB2012/050189 Patentability Report dated Jul. 16, 2013 (5 pages).

International Application PCT/IB2012/053149 Search Report dated Jan. 15, 2013 (2 pages).

U.S. Appl. No. 09/125,438 Official Action dated May 3, 1999 (4 pages).

U.S. Appl. No. 09/125,438 Official Action dated Jul. 15, 1999 (7 pages).

(56) References Cited

OTHER PUBLICATIONS

U.S. Appl. No. 10/535,103 Official Action dated Feb. 2, 2009 (9 pages).
European Application No. 05810500.8 Official Action dated Jul. 6, 2009 (5 pages).
European Application No. 05810500.8 Response to Official Action dated Jul. 6, 2009, submitted Oct. 15, 2009 (8 pages).
European Application No. 05810500.8 Official Action dated Jan. 23, 2012 (4 pages).
European Application No. 05810500.8 Response to Official Action dated Jan. 23, 2012, submitted May 22, 2012 (6 pages).
U.S. Appl. No. 11/791,599 Official Action (Non-Final) dated Aug. 19, 2010 (16 pages).
U.S. Appl. No. 11/791,599 Response to Official Action (Non-Final) dated Aug. 19, 2010, submitted Jan. 11, 2011 (8 pages).
U.S. Appl. No. 11/791,599 Official Action (Final) dated Mar. 31, 2011 (13 pages).
U.S. Appl. No. 11/791,599 Response to Official Action (Final) dated Mar. 31, 2011, submitted May 23, 2011 (7 pages).
U.S. Appl. No. 11/791,599 Notice of Allowance issued Jun. 14, 2011 (5 pages).
U.S. Appl. No. 13/229,798 Official Action (Non-Final) dated Dec. 26, 2012 (10 pages).
U.S. Appl. No. 13/229,798 Response to Official Action (Non-Final) dated Dec. 26, 2012, submitted Mar. 21, 2013 (13 pages).
U.S. Appl. No. 13/229,798 Notice of Allowance issued Apr. 19, 2013 (6 pages).
U.S. Appl. No. 13/229,798 Notice of Withdrawal from Issue dated May 13, 2013 (1 page).
U.S. Appl. No. 13/229,798 Official Action (Non-Final) dated Jun. 21, 2013 (6 pages).
Chinese Patent Application No. 200580045471.3 "Finger-type peristaltic pump" Official Action dated Jul. 18, 2008 and English translation thereof (7 pages).
Chinese Patent Application No. 200780041966.8 Official Action dated Jul. 13, 2010 (7 pages).
Chinese Patent Application No. 200780041966.8 Response to Official Action dated Jul. 13, 2010, as submitted (6 pages).
Chinese Patent Application No. 200780041966.8, translation of Notification of Grant, issued Jan. 28, 2011 (2 pages).
U.S. Appl. No. 12/464,202 Official Action (Non-Final) dated Oct. 3, 2011 (7 pages).
U.S. Appl. No. 12/464,202 Response to Official Action (Non-Final) dated Oct. 3, 2011, submitted Feb. 12, 2012 (12 pages).
U.S. Appl. No. 12/464,202 Notice of Allowance issued Jul. 11, 2012 (5 pages).
U.S. Appl. No. 13/651,420 Official Action (Non-Final) dated Jan. 6, 2014 (8 pages).
U.S. Appl. No. 13/651,420 Response to Official Action (Non-Final) dated Jan. 6, 2014, submitted Mar. 5, 2014 (9 pages).
U.S. Appl. No. 13/651,420 Official Action (Final) dated Apr. 24, 2014 (8 pages).
U.S. Appl. No. 13/651,420 Response to Official Action (Final) dated Apr. 24, 2014, submitted Jul. 22, 2014 with Request for Continued Examination (15 pages).
U.S. Appl. No. 13/651,420 Official Action (Non-Final) dated Aug. 19, 2014 (10 pages).
U.S. Appl. No. 13/651,420 Response to Official Action (Non-Final) dated Aug. 19, 2014, submitted Dec. 18, 2014 (7 pages).
U.S. Appl. No. 14/016,105 Official Action (Non-Final) dated Oct. 15, 2014 (10 pages).
U.S. Appl. No. 13/681,440 Response to Official Action (Non-Final) dated Oct. 24, 2013, submitted Jan. 20, 2014 (10 pages).
U.S. Appl. No. 13/681,440 Official Action (Final) dated Feb. 14, 2014 (14 pages).
U.S. Appl. No. 13/681,440 Response to Official Action (Final) dated Feb. 14, 2014, submitted Jul. 14, 2014 with Request for Continued Examination (14 pages).
U.S. Appl. No. 13/681,440 Official Action (Non-Final) dated Sep. 2, 2014 (19 pages).
U.S. Appl. No. 12/514,311 Official Action (Non-Final) dated Oct. 7, 2014 (11 pages).
U.S. Appl. No. 13/742,454 Response to Official Action (Non-Final) dated Oct. 7, 2013, submitted Jan. 6, 2014 (7 pages).
U.S. Appl. No. 13/742,454 Official Action (Final) dated Mar. 28, 2014 (14 pages).
U.S. Appl. No. 13/742,454 Response to Official Action (Final) dated Mar. 28, 2014, submitted Jun. 29, 2014 with Request for Continued Examination (10 pages).
U.S. Appl. No. 13/742,454 Notice of Allowance issued Aug. 21, 2014 (10 pages).
U.S. Appl. No. 13/640,519 Official Action (Non-Final) dated Dec. 24, 2013 (7 pages).
U.S. Appl. No. 13/640,519 Response to Official Action (Non-Final) dated Dec. 24, 2013, submitted Jan. 16, 2014 (2 pages).
U.S. Appl. No. 13/640,519 Official Action (Non-Final) dated Mar. 20, 2014 (15 pages).
U.S. Appl. No. 13/640,519 Response to Official Action (Non-Final) dated Mar. 20, 2014, submitted Jun. 17, 2014 (14 pages).
U.S. Appl. No. 13/640,519 Official Action (Final) dated Oct. 1, 2014 (11 pages).
U.S. Appl. No. 13/924,572 Official Action (Non-Final) dated Dec. 2, 2014 (13 pages).
European Application No. 11768544.6 Supplementary Partial European Search Report dated Nov. 13, 2014 (7 pages).
European Application No. 12734200.4 Supplementary European Search Report dated Aug. 18, 2014 (6 pages).
U.S. Appl. No. 12/463,399 Official Action (Non-Final) dated Jul. 21, 2011 (15 pages).
U.S. Appl. No. 12/463,399 Response to Official Action (Non-Final) dated Jul. 21, 2011, submitted Oct. 21, 2011 (5 pages).
U.S. Appl. No. 12/463,399 Official Action (Final) dated Dec. 13, 2011 (7 pages).
U.S. Appl. No. 12/463,399 Response to Official Action (Final) dated Dec. 13, 2011, submitted Feb. 12, 2012 (10 pages).
U.S. Appl. No. 12/463,399 Advisory Action and Applicant Initiated Interview Summary dated Mar. 8, 2012 (8 pages).
U.S. Appl. No. 12/463,399 Response to Official Action (Final) dated Dec. 13, 2011, submitted Mar. 26, 2012 with Request for Continued Examination (13 pages).
U.S. Appl. No. 12/463,399 Notice of Allowance issued Apr. 29, 2013 (14 pages).
U.S. Appl. No. 12/514,310 Official Action (Non-Final) dated Jul. 21, 2011 (8 pages).
U.S. Appl. No. 12/514,310 Response to Official Action (Non-Final) dated Jul. 21, 2011, submitted Oct. 21, 2011 (8 pages).
U.S. Appl. No. 12/514,310 Official Action (Final) dated Jan. 20, 2012 (10 pages).
U.S. Appl. No. 12/514,310 Response to Official Action (Final) dated Jan. 20, 2012, submitted Apr. 25, 2012 with Request for Continued Examination (11 pages).
U.S. Appl. No. 12/514,310 Official Action (Non-Final) dated May 25, 2012 (7 pages).
U.S. Appl. No. 12/514,310 Response to Official Action (Non-Final) dated May 25, 2012, submitted Jun. 28, 2012 (6 pages).
U.S. Appl. No. 12/514,310 Notice of Allowance issued Aug. 22, 2012 (7 pages).
U.S. Appl. No. 12/514,311 Official Action (Non-Final) dated Sep. 16, 2010 (10 pages).
U.S. Appl. No. 12/514,311 Response to Official Action (Non-Final) dated Sep. 16, 2010, submitted Dec. 9, 2010 (23 pages).
U.S. Appl. No. 12/514,311 Official Action (Final) dated Feb. 18, 2011 (7 pages).
U.S. Appl. No. 12/514,311 Examiner Interview Summary Record dated Mar. 4, 2011 (4 pages).
U.S. Appl. No. 12/514,311 Response to Official Action (Final) dated Feb. 18, 2011, submitted Mar. 31, 2011 with Request for Continued Examination (9 pages).
European Patent Application No. 10192477.7 Search Report dated May 10, 2011 (5 pages).
European Patent Application No. 10192477.7 Response to Search Report dated May 10, 2011, submitted Dec. 28, 2011.

(56) References Cited

OTHER PUBLICATIONS

U.S. Appl. No. 12/644,026 Official Action (Non-Final) dated Apr. 6, 2012 (12 pages).
U.S. Appl. No. 12/644,026 Response to Official Action (Non-Final) dated Apr. 6, 2012, submitted Jul. 5, 2012 (11 pages).
U.S. Appl. No. 12/644,026 Notice of Allowance issued Oct. 11, 2012 (10 pages).
U.S. Appl. No. 13/742,454 Official Action (Non-Final) dated Oct. 7, 2013 (13 pages).
U.S. Appl. No. 12/644,027 Official Action (Non-Final) dated Apr. 28, 2011 (7 pages).
U.S. Appl. No. 12/644,027 Response to Official Action (Non-Final) dated Apr. 28, 2011, submitted Jul. 21, 2011 (10 pages).
U.S. Appl. No. 12/644,027 Notice of Allowance issued Nov. 17, 2011 (5 pages).
PCT Appl. No. PCT/IB14/62106 International Search Report and Written Opinion dated Feb. 24, 2015 (8 pages).
European Application No. 05810500.8 Response to Official Action dated Nov. 3, 2014, submitted Mar. 9, 2015 (31 pages).
European Application No. 12805094.5 Supplementary European Search Report dated Feb. 23, 2015 (8 pages).
U.S. Appl. No. 14/016,105 Notice of Allowance issued Feb. 17, 2015 (33 pages).
U.S. Appl. No. 14/181,673 Official Action (Non-Final) dated Jun. 3, 2015 (20 pages).
U.S. Appl. No. 13/651,420 Official Action (Final) dated Jun. 9, 2015 (18 pages).
U.S. Appl. No. 13/681,440 Official Action (Final) dated Apr. 24, 2015 (30 pages).
European Application No. 11768544.6 Response to Official Action dated Dec. 2, 2014, submitted May 29, 2015 (12 pages).
U.S. Appl. No. 12/514,311 Official Action (Final) dated Apr. 20, 2015 (26 pages).
U.S. Appl. No. 13/978,538 Official Action (Non-Final) dated Jan. 23, 2015 (24 pages).
PCT Appl. No. PCT/IB15/50873 International Search Report and Written Opinion dated Jun. 25, 2015 (8 pages).
European Application No. 12805094.5 Supplementary European Search Report dated Jun. 30, 2015 (14 pages).
U.S. Appl. No. 13/759,181 Examiner's search strategy and results dated Jul. 6, 2015 (1 page).
U.S. Appl. No. 13/978,538 Response to Official Action (Non-Final) dated Jan. 23, 2015, submitted May 21, 2015 (13 pages).
European Application No. 05810500.8 Official Action dated Nov. 3, 2014 (5 pages).
Indian Patent Application No. 2344KOLNP2007 Office Action dated Dec. 31, 2014 (2 pages).
Indian Patent Application No. 2344KOLNP2007 Response to Office Action dated Dec. 31, 2014, submitted Aug. 7, 2015 (19 pages).
U.S. Appl. No. 14/181,673 Official Action (Non-Final) dated Jun. 3, 2015 (12 pages).
U.S. Appl. No. 13/651,420 Official Action (Final) dated Mar. 16, 2015 (6 pages).
U.S. Appl. No. 13/651,420 Response to Official Action (Final) dated Mar. 16, 2015, submitted May 14, 2015 (5 pages).
U.S. Appl. No. 13/651,420 Official Action (Final) dated Jun. 9, 2015 (9 pages).
U.S. Appl. No. 14/016,105 Response to Official Action (Non-Final) dated Oct. 15, 2014, submitted Jan. 14, 2015 (7 pages).
U.S. Appl. No. 14/016,105 Notice of Allowance dated Feb. 17, 2015 (14 pages).
U.S. Appl. No. 13/681,440 Response to Official Action (Non-Final) dated Sep. 2, 2014, submitted Feb. 25, 2015 (12 pages).
U.S. Appl. No. 13/681,440 Official Action (Final) dated Apr. 24, 2015 (21 pages).
U.S. Appl. No. 12/514,311 Response to Official Action (Non-Final) dated Oct. 7, 2014, submitted Jan. 7, 2015 (5 pages).
U.S. Appl. No. 12/514,311 Official Action (Final) dated Apr. 20, 2015 (12 pages).
U.S. Appl. No. 12/514,311 Response to Official Action (Final) dated Apr. 20, 2015, submitted Jun. 21, 2015 (10 pages).
U.S. Appl. No. 12/514,311 Official Action (Advisory Action) dated Jul. 1, 2015 (8 pages).
U.S. Appl. No. 12/514,311 Response to Official Action (Advisory Action) dated Jul. 1, 2015, submitted Jul. 20, 2015 (8 pages).
U.S. Appl. No. 12/514,311 Official Action (Advisory Action) dated Aug. 5, 2015 (6 pages).
European Application No. 10192477.7 Official Action dated Jul. 6, 2015 (5 pages).
U.S. Appl. No. 13/640,519 Response to Official Action (Final) dated Oct. 1, 2014, submitted Dec. 28, 2014 (15 pages).
U.S. Appl. No. 13/640,519 Official Action (Non-Final) dated May 6, 2015 (13 pages).
European Application No. 12734200.4 Response to Official Communication dated Sep. 4, 2014, submitted Mar. 4, 2015 (16 pages).
U.S. Appl. No. 13/978,538 Official Action (Non-Final) dated Jul. 24, 2015 (16 pages).
European Application No. 12805094.5 Supplementary Partial European Search Report dated Feb. 23, 2015 (8 pages).
European Application No. 12805094.5 Response to Supplementary Partial European Search Report submitted Apr. 2, 2015 (1 page).
U.S. Appl. No. 13/924,572 Response to Official Action (Non-Final) dated Dec. 2, 2014, submitted Mar. 26, 2015 (11 pages).
U.S. Appl. No. 13/924,572 Official Action (Non-Final) dated May 14, 2015 (12 pages).

\* cited by examiner

FINGER-TYPE PERISTALTIC PUMP

CROSS REFERENCE TO RELATED APPLICATIONS

The present application is a Continuation Application of U.S. patent application Ser. No. 13/229,798, filed on Sep. 12, 2011, which '798 application is a Continuation Application of U.S. patent application Ser. No. 11/791,599, filed on May 24th, 2007, which '599 application is a National Stage Application of PCT Application No. PCT/IL2005/001249, filed Nov. 24, 2005, which claims priority from Israeli Patent Application No. 165365, filed Nov. 24, 2004. Each of the aforementioned applications is hereby incorporated into this application by reference in its entirety.

FIELD OF THE INVENTION

The present invention relates to pumps and more specifically to finger-type peristaltic pumps.

BACKGROUND OF THE INVENTION

Peristaltic pumps are used for creating a flow of a fluid in an elastic tubular conduit. These pumps have many medical and industrial applications.

In one form of peristaltic pumps, a rotor is used to rotate a plurality of eccentric cams. Each cam, in turn, intermittently collapses the elastic conduit at an initial contact point, and slides along the conduit over a short distance as the rotor turns. A second cam contacts the initial contact point, and the first cam is then released from the conduit as the second cam slides along the conduit. As this process is repeated, a flow of fluid in the conduit is generated in the direction of the sliding of the cams.

In another form of peristaltic pumps referred to herein as a "finger-type peristaltic pump", a series of valves is aligned along an elastic conduit. Each valve comprises a "finger" that can alternate between two positions. In one position, the finger is extended from the valve so as to contact the conduit and to at least partially occlude the conduit at the point of contact. In the other position, the finger is retracted and does not contact the conduit. The series of valves is operated according to a temporo-spatial pattern so as to generate a flow in the conduit.

Commercially-available finger-type peristaltic pumps essentially include a hinged door, which is usually a rotatable member, adapted to continuously press the fluid conduit inserted in the body towards the valve fingers located in the body when it is closed configuration. This door is a frequent cause of failure in the pump's operation: the door is frequently opened while the pump is in action, thus causing the conduit to fall out of place and cease pumping, opening the door and holding it open so as to insert the pipe requires three pairs of hands and thus can only be performed by two persons together necessitating the presence of two medical personnel.

In addition, in this configuration the conduit pipe is exposed, i.e; is not wrapped or coated in any other material and is thus more vulnerable to contamination. The pipe is normally made of thin flexible silicone, which is worn down by the tip of the finger pump during extended use. Since it is common hospital practice to make use of a single pipe during the course of a patient's hospitalization, without replacing the pipe, during the course of use the pipe becomes increasingly vulnerable to puncturing, thus enabling contaminants (such as blood, HIV, Hepatitis virus, radioactive medicaments etc.) which may be present in the patients bloodstream or in the infusion being delivered, to accumulate on the outer surface of the pipe. If the pipe is inadvertently touched by unprotected hospital personnel, the user himself or his visitors, such contaminants may rapidly spread and be transmitted to a wider population.

The configurations currently available comprise three separate components: body, conduit and door. Inserting the conduit into the body, and then closing the door accurately requires considerable experience and manual dexterity, and can not normally be performed by chronically ill, physically limited or geriatric patients independently, thus requiring the constant attention of hospital personnel.

U.S. Pat. No. 5,395,320 to Padda et al. teaches a programmable peristaltic fingers infusion pump with an interchangeable variety of disposable tubing in commonly available sizes and types. The pump essentially comprises no less than two doors: an outer door (1) and an inner door (20), wherein the outer door (1) protects the inner door (20), which is kept in a close configuration by door latch (2).

U.S. Pat. No. 5,807,322 to Lindsey et al. presents a peristaltic pump unit that has a flexible infusion line (28) which is repeatedly compressed by a pusher (30). Line (28) is positioned in an elongated groove or channel (58) which acts to restrain sideways bulging of the line as it is being compressed by the pusher. The patent teaches that peristaltic pumps may be associated with a cassette which acts as a reservoir for the fluid to be pumped.

FR 2,753,236 to Ray et al. introduces a miniature peristaltic pump. The pump comprises inter alia a rotor, and a support piece equipped with a rounded-off portion (308) arranged in a substantially concentric manner to the rotor and against which, during operation, said rollers compress a flexible tubing (202) connected to a solution reservoir (201). Tubing (202) is inserted into circular opening (310), closed off by a cover (311). Thus again, slidable door member (311) ensures conduit (202) location directly adjacent to the pumping effecters (here rollers 110). Again the body and the door are integrally attached.

FR 2,632,529 to Gautier et al. teaches a drug injector with a removable reservoir in which the infusion liquid container may be inserted- held to control box by a pivoting arm engaged by head. The patent discloses a pump having a body (2) and rotatable pumping effecter (pump drum 7) towards which pipe (4) is pressed by means of maneuverable arm (10) being interconnected to body (2) by an hinge. Arm (10) is forcefully secured to body (2) by screw (16).

SUMMARY OF THE INVENTION

The present invention provides a finger-type peristaltic pump. The pump of the invention may be used, for example, in a medical context for infusing a liquid into the body of a subject.

The peristaltic pump of the invention comprises a housing for holding a segment of an elastic conduit adjacent to the fingers of the valves of the pump. In one embodiment, the housing is hinged at one end to the body of the pump. The housing is swung out from the body in order to introduce a segment of an elastic conduit into the housing. The housing is then swung back towards the body so as to position the conduit segment adjacent to the fingers of valves of the pump. The housing may be maintained in this closed position by a snapping mechanism, or by a latch.

In another embodiment, the housing of the invention is detachable from the body of the pump. A segment of a conduit may be introduced into the housing when the housing is detached. The housing is then attached onto the body of the pump so as to position the segment of the conduit adjacent to the valve fingers. In a most preferred embodiment, the housing is integral with a segment of a conduit. In this case, the conduit in the housing has fittings at each end allowing the conduit to be attached at each end to another piece of conduit, so that the pump may be integrated into a pumping system. In the detachable housing embodiment, the housing may be disposable.

The housing of the invention preferably includes an anti-free-flow mechanism to prevent the flow of fluid in the segment of the conduit in the housing when the conduit is not adjacent to the fingers. The antifree-flow has a non-obstructing position in which the antifree-flow device does not prevent flow in the conduit, and an obstructing position in which the antifree-flow device prevents flow in the conduit. The antifree-flow device is spring biased in the obstructing position, so that when the housing is swung away or detached from the body of the pump, the antifree-flow device spontaneously assumes its obstructing position. This prevents unintentional flow in the conduit when the housing is swung out or detached from the body of the pump. The antifree-flow device preferably includes an override mechanism that allows the antifree-flow device to be temporarily latched in its non-obstructing position when the housing is swung away or detached from the body in order to allow a segment of conduit to be introduced into the housing. As the housing is brought to its position in which it is attached to the pump, the antifree-flow device is brought to its unlatched non-obstructing position, regardless of whether it was previously in its obstructing position or its latched non-obstructing position. The antifree flow device may prevent flow in the conduit in both directions or only in one direction.

Thus, in its first aspect, the invention provides a finger-type peristaltic pump comprising a body and a housing, the body containing two or more finger-type valves and a processor configured to operate the valves according to a predetermined temporo-spatial pattern, the housing having a passageway configured to receive a conduit, the housing having a first position in which a conduit in the passageway is positioned adjacent to the valve fingers, and a second position in which a conduit in the passageway is not adjacent to the valve fingers.

In its second aspect, the invention provides a housing for use in the pump of the invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1A:
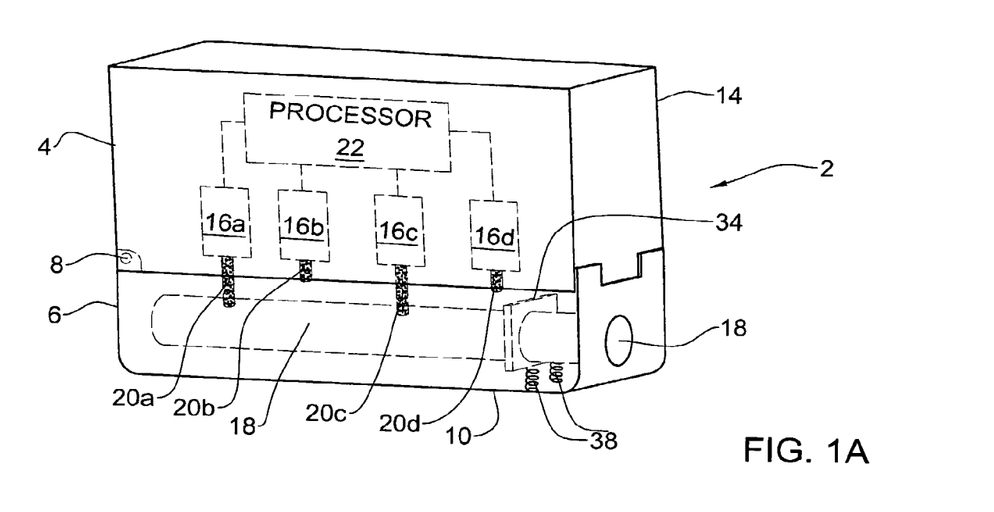
FIGS. 1A and 1B show a peristaltic pump having a housing in a closed position and in an open position (respectively) in accordance with one embodiment of the invention.
Figure 1B:
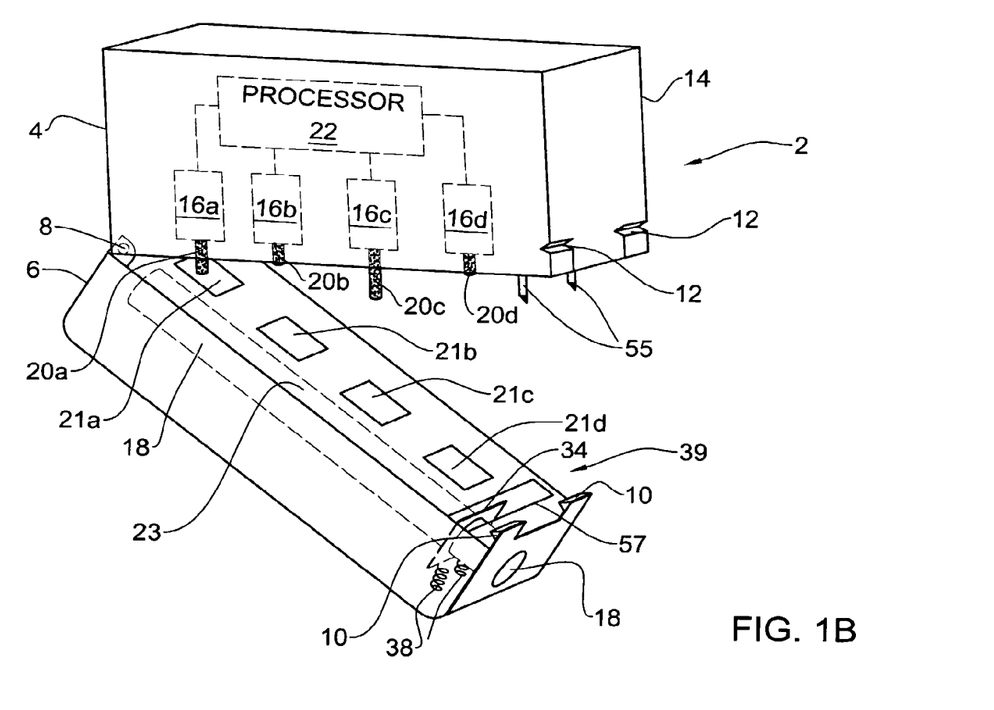

FIG. 1 shows a finger-type peristaltic pump 2 in accordance with one embodiment of the invention. The pump 2 has a body 4 and a housing 6. The housing 6 is hinged to the body 4 at a hinge 8 so as to allow the housing 6 to pivot between a closed position shown in FIG. 1a and an open position shown in FIG. 1b. The housing 6 snaps into the closed position by means of projections 10 located at the end of the housing 6 distal to the hinge 8 that snaps into mated notches 12 in the body 4.

The housing 6 has a passageway 18 dimensioned to receive a segment of an elastic conduit as explained below.

The body 4 has a housing 14 containing a plurality of electrically operated valves 16. Four valves, 16a to 16d, are shown in FIG. 1. This is by way of example only and the pump may have any number of valves 16 greater than two. Each valve 16 has a respective finger 20. Each valve 16 is electrically operable to oscillate its finger 20 from a retracted position in which the finger 20 does not contact a conduit in the passageway 18 and an extended position in which the finger 20 at least partially occludes a flexible conduit in the passageway 18. The fingers 20b and 20d are shown in FIG. 1 in their retracted position, while the fingers 20a and 20d are shown in FIG. 1 in their extended position. Each finger 20 corresponds to a finger hole 21 in the upper surface 23 of the housing 6. A finger 16, when in its extended position, extends through its respective finger hole 20 into the housing 6 to compress a region of a conduit in the passageway 18.

The body 4 also contains a processor 22 configured to operate the valves 16 according to a temporo-spatial pattern so as to generate a flow of fluid in an elastic conduit in the passageway 18 when the housing 6 is in its closed position shown in FIG. 1a, as is known in the art.

Figure 2:
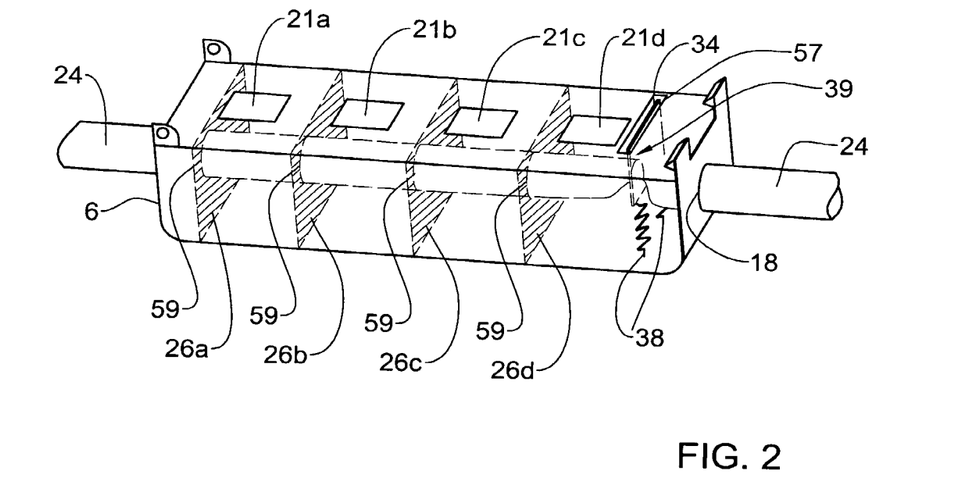
FIG. 2 shows the housing of the peristaltic pump of FIG. 1.

FIG. 2 shows the housing 6 in greater detail. A conduit 24 made from an elastic material has been introduced into the passageway 18. The conduit 24 is supported in the passage 18 by one or more supports 26 that prevent bulging of the conduit 24 between two fingers 20 in the extended state. The supports 26 also prevent lateral movement of the conduit 24 in the passageway 18 during operation of the pump. The cross sectional shape of the passageway 18 is determined by the shape of holes 59 in the supports 26

Figure 3:
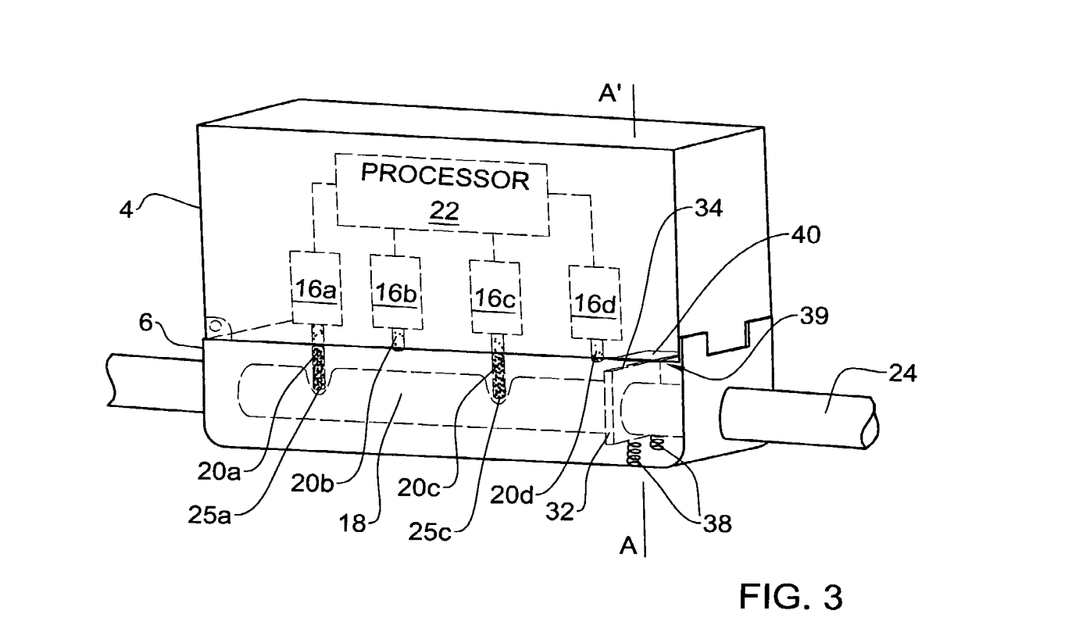
FIG. 3 shows the peristaltic pump of FIG. 1 together with a conduit.

FIG. 3 shows the pump 2 with a conduit 24 in the passageway 18 in its closed position shown also in FIG. 1a. As can be seen, the fingers 20a and 20c are in their extended position and therefore constrict the conduit 24 and the points of contact 25a and 25c. As explained above, the valves 16 are operated by the processor 22 so that the fingers 20 alternate between their retracted and extended positions so as to generate a flow in the conduit 24

Figure 4A:
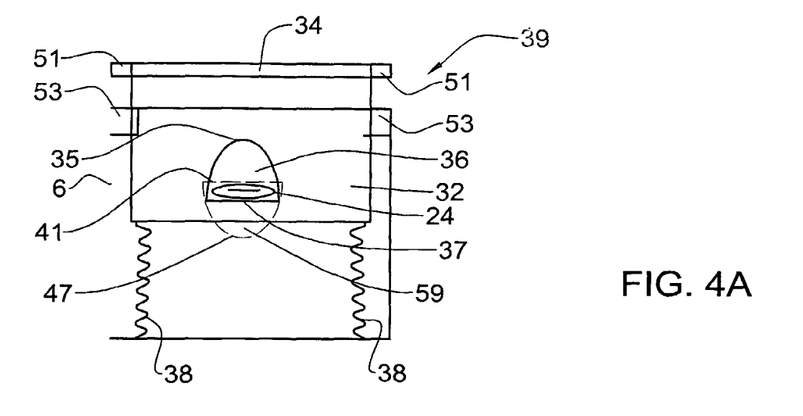
FIGS. 4A, 4B and 4C show an anti free flow device for use in the housing, of FIG. 3 wherein an occlusion plate is in an obstructing position, a non-obstructing position and a latched non-obstructing position (respectively)
Figure 4B:
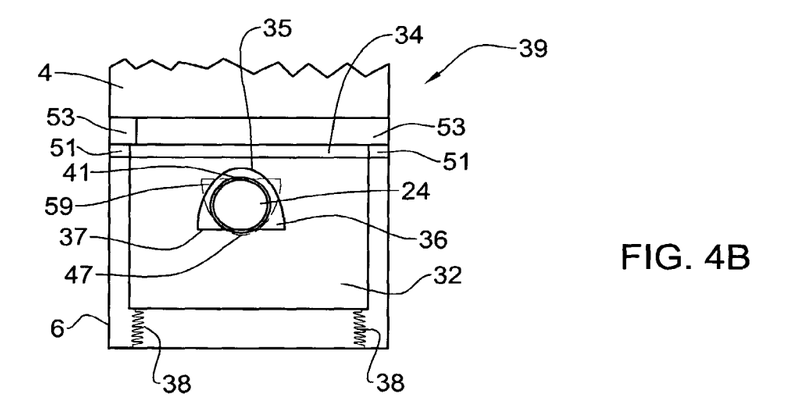

The housing 6 includes an anti-free flow mechanism 39. The anti-free flow mechanism prevents the flow of fluid in the conduit 24 when the housing 6 is not in its closed position shown in FIG. 1a. The anti-free flow mechanism is shown in FIG. 4 in a cross section AA' of the pump 2 shown in FIG. 3. The housing 6 is shown in its open position in FIG. 4a and in its closed position in FIG. 4b. The anti-free flow includes an occlusion plate 32, from which an actuating tab 34 extends (see also FIGS. 1 and 2). The occluding plate 32 has a D-shaped hole 36 having a straight bottom edge 37 and an upper arcuate edge 35. A hole 59 of the passageway 18 is indicated in FIG. 4 by a broken line. The holes 59 of the passageway 18 are "D" shaped, having a straight upper edge 41 and an arcuate lower edge 47. The occluding plate is slidable from an obstructing position shown in FIG. 4a and a non-obstructing position shown in FIG. 4b. The occluding plate 32 is spring biased in its obstructing position by means of springs 38. In its non-obstructing position (FIG. 4b), the hole 36 of the occlusion plate 32 is essentially aligned with the passageway 18 so that the conduit 24 is unobstructed. In its obstructing position (FIG. 4a), the hole 36 and the passageway 18 only partially overlap, so that the conduit 24 is collapsed between the straight edge 37 of the hole 36 and the straight edge 41 of the passageway 18. The conduit 24 is thus obstructed, as shown in FIG. 4a. This prevents unintentional flow of fluid in the conduit 24 when the housing 6 is swung out from the body 4.

Figure 4C:
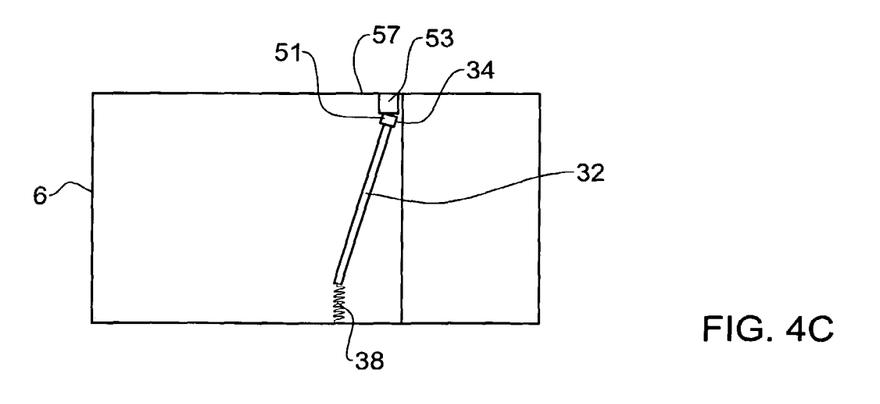

When the housing 6 is swung out from the body 4, the obstructing plate 32 may be brought into its non-obstructing position (FIG. 4b) by manually depressing the tab 34. The tab 34 may be temporarily latched with the plate 32 in its non-obstructing position. This may be done for example, when it is desired to allow free flow of fluid in the conduit. The plate 32 in its latched non-obstructing position is shown in a side view in FIG. 4c. Extensions 51 on either side of the tab 34 (see also FIGS. 4a and 4b) are lodged under extensions 53 of the inner wall of the housing 6. The obstructing plate 32 is brought into its latched non-obstructing position (FIG. 4a) from its unlatched non-obstructing position (FIG. 4b) by rotating the plate 32 so as to lodge the extensions 51 under the extensions 53. An upwards pressure on the plate 32 by the springs 38 presses the extensions 51 onto the extensions 53 so as to maintain the anti-free-flow mechanism in its latched non-obstructing state. The obstructing plate 32 may be manually released from its lodged, non-obstructing position by rotating the plate 32 back so as to dislodge the extensions 51 from under the extensions 53. The plate 32 then passes through a slot 57 in the housing 6 in order to regain its obstructing position (FIG. 4a) under the influence of the spring 38. The housing 6 is then swung shut onto the body 4 (FIG. 4b). If the anti-free flow mechanism is in its latched non-obstructing position when the housing is swung onto the body 4, a pair of wedges 55 extending from the body 4 (FIG. 1b) rotate the plate 32 as the housing 6 is being swung shut so as to dislodge the extensions 51 from under the extensions 53. A static plate 40 fixed in the body 4 depresses the tab 34 against the spring 38 so to maintain the plate 32 in its unlatched non-obstructing position when the housing 6 is in its closed position.

Figure 5A:
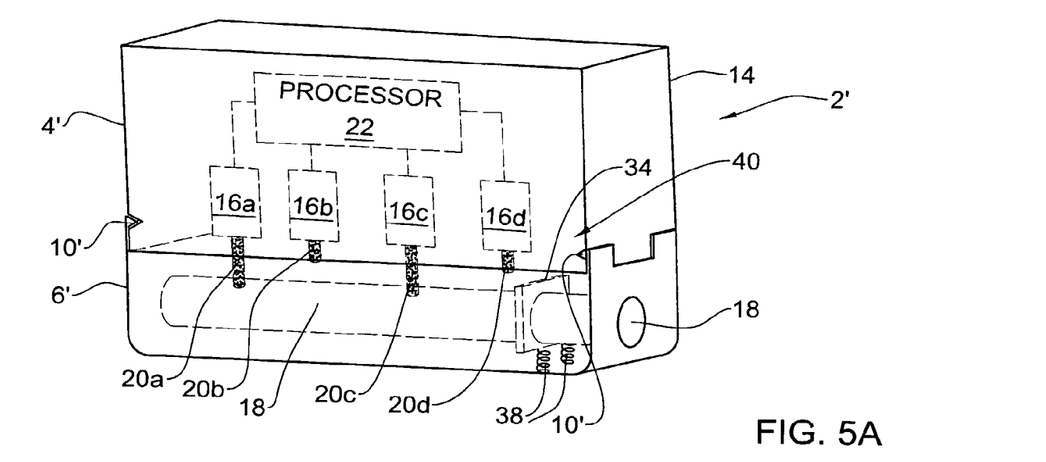
FIGS. 5A and 5B show a peristaltic pump having a housing, wherein the housing is attached or detached from the peristaltic pump body (respectively) in accordance with another embodiment of the invention.
Figure 5B:
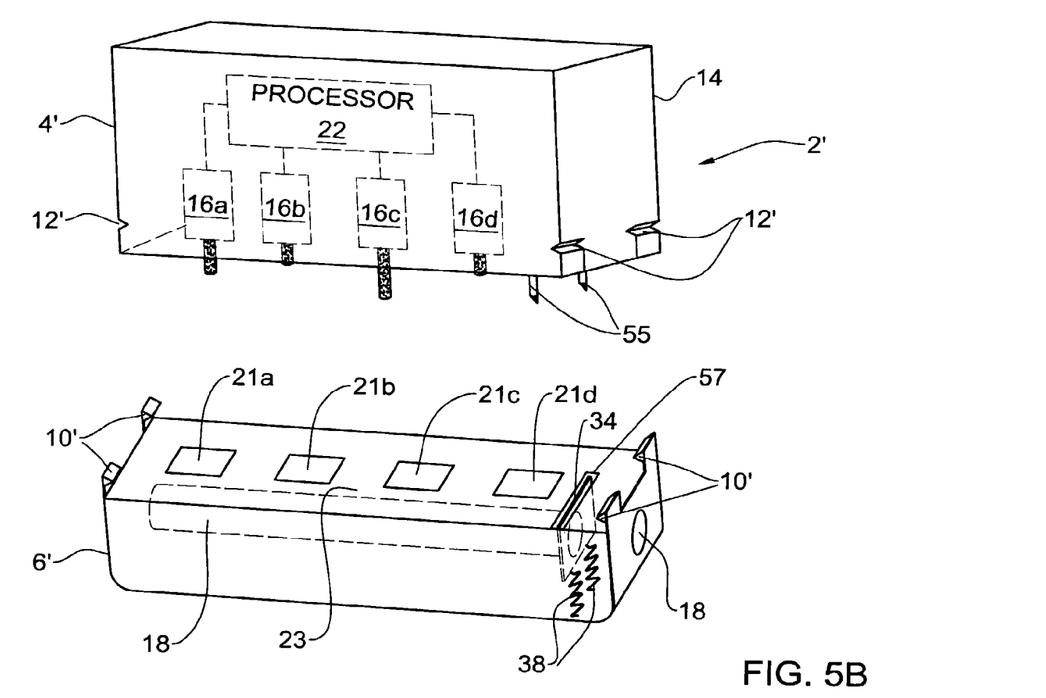

FIG. 5 shows a finger-type peristaltic pump 2' in accordance with another embodiment of the invention. Components of the pump 2' similar to components of the pump 2 are designated by the same reference numerals without further comment. The pump 2' has a body 4' and a housing 6'. The housing 6' is reversibly attachable to the body 4' by means of projections 10' located at both ends of the housing 6' that snap into mated notches 12' on opposite sides of the body 4'. In FIG. 5a, the housing 6' is shown attached to the body 4', and in FIG. 5b, the housing 6' is shown detached from the body 4'. The pump 2' is operated as described above in reference to the pump 2. The housing 6' may be disposable.

Figures 6, 7:
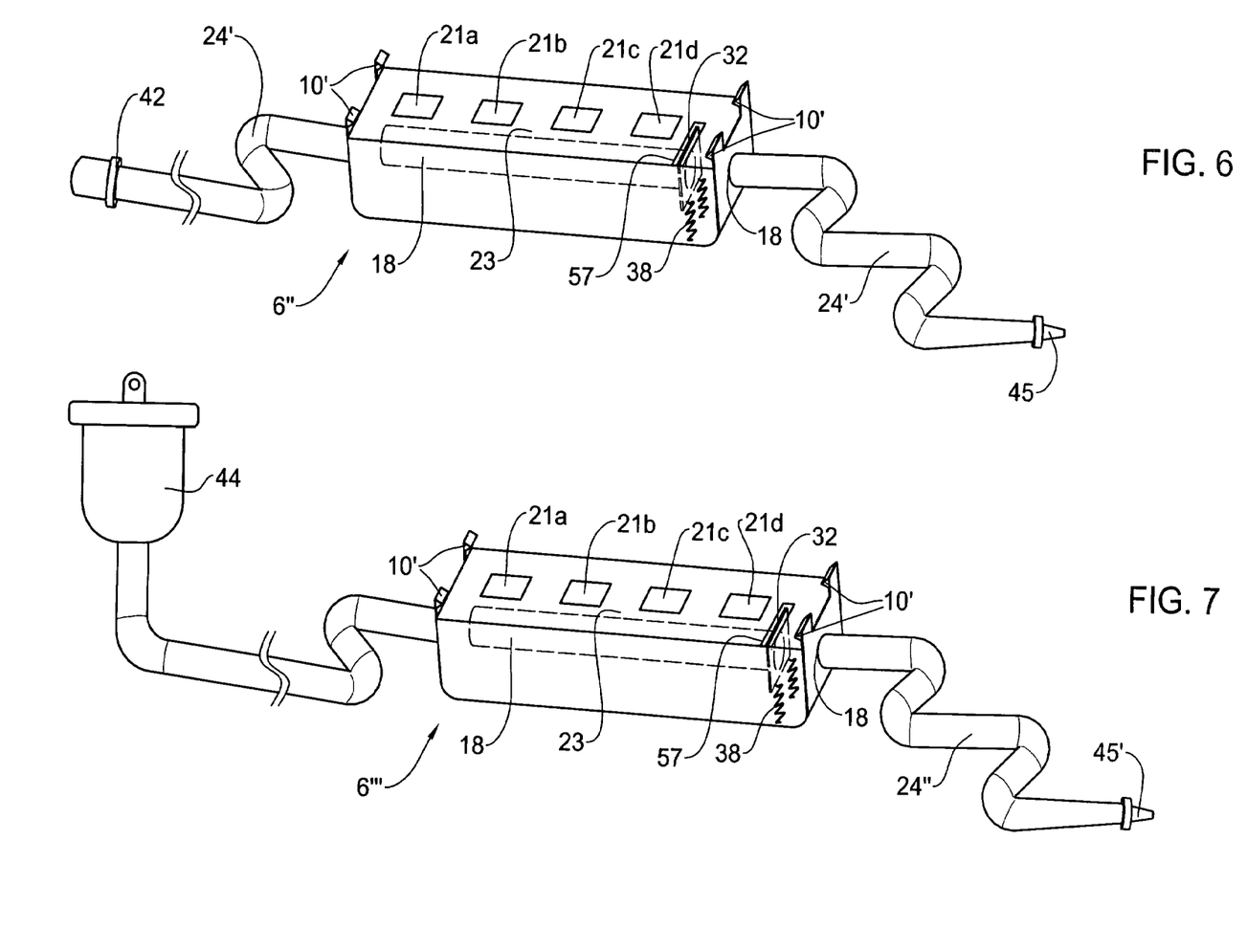
FIG. 6 shows a housing for use in the peristaltic pump of FIG. 5 integral with a conduit.
FIG. 7 shows a housing for use in the peristaltic pump of FIG. 5 integral with a conduit and a fluid reservoir.

FIG. 6 shows a housing 6" that may be used with the body 4' instead of the housing 6'. Components of the housing 6" similar to components of the housing 6' are designated by the same reference numerals without further comment. The housing 6" is integral with an elastic conduit 24'. The conduit 24' is provided at one end with a connector 42 suitable for forming a fluid connection with an upstream fluid reservoir, such as an infusion bag (not shown). The other end of the conduit 24' is provided with a connector 45 for forming a fluid connection with a downstream device, such as a needle (not shown).

FIG. 7 shows a housing 6''' that may be used with the body 4' instead of the housing 6'. Components of the housing 6''' similar to components of the housing 6' are designated by the same reference numerals without further comment. The housing 6''' is integral with an elastic conduit 24". The conduit 24" is integral with an upstream fluid reservoir, such as an infusion bag 44. The other end of the conduit 24" is provided with a connector 45' for forming a fluid connection with a downstream device, such as a needle (not shown).

The invention claimed is:

1. An apparatus comprising:
   a conduit housing including a tube segment;
   one or more pump interlock elements adapted to facilitate detachable engagement of the housing with a peristaltic pump;
   an anti-free-flow mechanism having a first default state which obstructs flow through the tube segment when the housing is detached from the pump and a second mechanically latched override state which allows fluid to flow through the tube segment when the housing is detached; and
   a third engaged default state wherein said anti-free flow mechanism is brought into the third state when the housing is attached to the pump, from (a) the first default state if the anti-free-flow mechanism is in the first default state when the housing is detached from the pump and from (b) the second mechanically latched override state if the anti-free-flow mechanism is in the second mechanically latched override state when the housing is detached from the pump.

2. The apparatus according to claim 1, further comprising an anti-free-flow override mechanism engageable when the housing is detached from the pump, said override mechanism being configured to, when engaged, mechanically latch said anti-free-flow mechanism in the second mechanically latched override state allowing fluid to flow through the tube segment.

3. The apparatus of claim 2, wherein said override mechanism is configured to automatically disengage when the housing is attached to the pump.

4. The apparatus of claim 1, wherein said anti-free-flow mechanism is a spring biased occlusion plate.

5. The apparatus of claim 1, wherein said anti-free-flow mechanism obstructs flow in one direction.

6. The apparatus of claim 1, wherein said anti-free-flow mechanism obstructs flow in two directions.

7. The apparatus of claim 1, wherein said tube segment is a pipe segment.

8. The apparatus of claim 7, wherein said pipe segment includes silicone.

9. A system for pumping fluid comprising:
   a peristaltic pump; and
   a conduit housing including:
      (a) a flexible tube segment,
      (b) one or more pump interlock elements adapted to facilitate detachable engagement of said housing with said pump,
      (c) an anti-free-flow mechanism having a disengaged default state which obstructs flow through said tube segment when said housing is detached from said pump, and wherein the anti-free-flow mechanism is brought into an engaged default state, allowing fluid to flow through the channel, when said housing is attached to said pump and (d) an anti-free-flow override mechanism engageable when said housing is detached from said pump, said override mechanism being configured to bring said anti-free-flow mechanism to a mechanically latched non-obstructing state, wherein said anti free flow mechanism is configured to transition to said engaged default state from both said disengaged default state and said mechanically latched non-obstructing state.

10. The system according to claim 9, wherein said mechanically latched non-obstructing state is configured to allow fluid to flow through the channel.

11. The system of claim 9, wherein said override mechanism is configured to automatically disengage when said housing is attached to the pump.

12. The system of claim 9, wherein said anti-free-flow mechanism is a spring biased occlusion plate.

13. The system of claim 9, wherein said anti-free-flow mechanism obstructs flow in one direction.

14. The system of claim 9, wherein said anti-free-flow mechanism obstructs flow in two directions.

15. The system of claim 9, wherein said pump is a finger type peristaltic pump.

16. The housing of claim 9, wherein said tube segment is a pipe segment and has a first cross section shape.

17. A peristaltic pump comprising:

a pumping mechanism configured to induce flow of a fluid at least through a flexible segment within a detachable housing, wherein said pump-includes one or more interlock elements configured to facilitate detachable engagement of said pump with the housing and includes a releasing element configured to bring an anti-free-flow mechanism of the housing into a disengaged state which allows fluid to flow through the flexible segment, when the housing is attached to the pumping mechanism, wherein said releasing element is further adapted to automatically disengage an anti-free-flow override mechanism, which anti-free-flow override mechanism is engageable when said housing is detached from the pump, said override mechanism being configured to, when engaged, mechanically latch the anti-free-flow mechanism in a non-obstructing state allowing fluid to flow through the flexible segment.

* * * * *